United States Patent
Jeong et al.

(10) Patent No.: US 10,639,267 B2
(45) Date of Patent: May 5, 2020

(54) HIGH INTERNAL PHASE WATER-IN-OIL TYPE COSMETIC COMPOSITION

(71) Applicant: AMOREPACIFIC CORPORATION, Seoul (KR)

(72) Inventors: Choon Bok Jeong, Yongin-si (KR); Yu Jin Kang, Yongin-si (KR); Kyung Nam Kim, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 72 days.

(21) Appl. No.: 15/756,429

(22) PCT Filed: Sep. 1, 2016

(86) PCT No.: PCT/KR2016/009754
§ 371 (c)(1),
(2) Date: Feb. 28, 2018

(87) PCT Pub. No.: WO2017/039338
PCT Pub. Date: Mar. 9, 2017

(65) Prior Publication Data
US 2018/0250220 A1    Sep. 6, 2018

(30) Foreign Application Priority Data

Sep. 2, 2015   (KR) .................. 10-2015-0124174
Aug. 31, 2016  (KR) .................. 10-2016-0111368

(51) Int. Cl.
| | | |
|---|---|---|
| *A61K 8/891* | (2006.01) | |
| *A61K 8/362* | (2006.01) | |
| *A61K 8/29* | (2006.01) | |
| *A61Q 19/00* | (2006.01) | |
| *A61K 8/06* | (2006.01) | |
| *A61K 8/19* | (2006.01) | |
| *A61Q 1/02* | (2006.01) | |
| *A61K 8/27* | (2006.01) | |

(52) U.S. Cl.
CPC .............. *A61K 8/891* (2013.01); *A61K 8/064* (2013.01); *A61K 8/19* (2013.01); *A61K 8/27* (2013.01); *A61K 8/29* (2013.01); *A61K 8/362* (2013.01); *A61Q 1/02* (2013.01); *A61Q 19/007* (2013.01); *A61K 2800/43* (2013.01); *A61K 2800/436* (2013.01); *A61K 2800/48* (2013.01)

(58) Field of Classification Search
CPC . A61K 8/27; A61K 8/19; A61K 8/891; A61K 8/064; A61K 8/29; A61K 8/362; A61K 8/06; A61K 8/34; A61K 2800/436; A61K 2800/48; A61K 2800/43; A61Q 19/00; A61Q 19/007; A61Q 1/02
See application file for complete search history.

(56) References Cited

U.S. PATENT DOCUMENTS

| | | | | |
|---|---|---|---|---|
| 8,128,913 | B1 * | 3/2012 | Roszell ............ | A61K 8/8164 424/59 |
| 9,498,652 | B2 * | 11/2016 | Moussouni .......... | A61K 8/044 |
| 2006/0067960 | A1 * | 3/2006 | Russ .................. | A61K 8/8194 424/401 |
| 2006/0134035 | A1 * | 6/2006 | Zheng ................ | A61K 8/8111 424/64 |
| 2010/0008883 | A1 * | 1/2010 | Alwattari ........... | A61K 8/416 424/70.13 |
| 2011/0171148 | A1 * | 7/2011 | Jones ................ | A61K 8/29 424/59 |
| 2012/0016024 | A1 | 1/2012 | Ibe et al. | |
| 2013/0343801 | A1 * | 12/2013 | Sakuma ............. | A61K 8/891 401/143 |
| 2015/0056152 | A1 * | 2/2015 | Masuda ............. | C08F 283/122 424/63 |
| 2015/0174048 | A1 * | 6/2015 | Tachon .............. | A61K 8/25 424/489 |
| 2015/0208647 | A1 * | 7/2015 | Lull ................. | A61L 9/013 424/60 |

FOREIGN PATENT DOCUMENTS

| | | |
|---|---|---|
| JP | 61037710 SA | 2/1986 |
| JP | 017100357 HA | 4/1995 |
| JP | 2004269418 A | 9/2004 |
| JP | 2005314327 A | 11/2005 |
| JP | 2010248173 A | 11/2010 |
| JP | 2011511831 A | 4/2011 |
| JP | 2011207865 A | 10/2011 |
| JP | 2012224598 A | 11/2012 |
| JP | 2013071931 A | 4/2013 |
| JP | 2014004084 A | 1/2014 |
| JP | 2014024834 A | 2/2014 |
| JP | 2014172837 A | 9/2014 |
| JP | 2015063512 A | 4/2015 |
| JP | 2015137263 A | 7/2015 |
| KR | 10-2002-0011969 A | 2/2002 |

(Continued)

OTHER PUBLICATIONS

International Preliminary Report on Patentability for PCT/KR2016/009754, dated Mar. 6, 2018; 16 pages. (Year: 2018).*

(Continued)

*Primary Examiner* — Mark V Stevens
(74) *Attorney, Agent, or Firm* — Lucas & Mercanti, LLP

(57) ABSTRACT

The present invention provides a high internal phase water-in-oil type cosmetic composition which shows colors by containing pearl particles or aqueous pigments in an internal phase. The present invention employs a particular kind of emulsifier forming large emulsification particles in order to allow the pearls or pigments to stably exist in an aqueous phase as an internal phase, and employs particular kinds of dispersant and preservative in order to supplement the emulsifying power for emulsion formation, prevent the separation of the formulation, and improve fluidity. In addition, in order to increase the degree of surface filling of the composition, silicone oil and ester oil are contained in an oil phase component as an external phase, and are mixed at a weight ratio in a suitable range. The cosmetic composition of the present invention provides the various aesthetic and functional effects of the pearls by stabilizing the pearls in the internal phase.

6 Claims, 3 Drawing Sheets

(56) References Cited

FOREIGN PATENT DOCUMENTS

| | | | | |
|---|---|---|---|---|
| KR | 10-0582348 B1 | | 6/2006 | |
| KR | 10-2011-0048899 A | * | 5/2011 | ............. A61K 8/064 |
| KR | 10-2011-0049375 A | | 5/2011 | |
| KR | 10-2011-0056877 A | * | 5/2011 | ............... A61K 8/73 |
| KR | 10-2011-0059986 A | | 6/2011 | |
| KR | 10-2014-0000504 A | * | 1/2014 | ............... A61K 8/92 |
| KR | 10-2014-0055343 A | | 5/2014 | |
| KR | 10-1453617 B1 | | 10/2014 | |
| WO | 200051551 A2 | | 9/2000 | |
| WO | 2011065772 A2 | | 6/2011 | |

OTHER PUBLICATIONS

Shin-Etsu (Shin-Etsu Silicone, Silicone Products for Personal Care (2005), [Retrieved from internet <URL: https://www.shinetsusilicones.com/files/literature/Shin-Etsu%20Unique%20Materials%202010%2011_2.pdf >], 20 pages) (Year: 2005).*
International Search Report and Written Opinion for International Application No. PCT/KR2016/009754. (14 Pages) (dated Dec. 23, 2016).

* cited by examiner (a)　　　　　　(b)　　　　　　(c)

(a)  (b)  (c)

HIGH INTERNAL PHASE WATER-IN-OIL TYPE COSMETIC COMPOSITION

CROSS-REFERENCE TO RELATED APPLICATIONS

This application is a 371 of PCT/KR2016/009754, filed Sep. 1, 2016 which claims the benefit of Korean Patent Application No. 10-2015-0124174, filed Sep. 2, 2015 and Korean Patent Application No. 10-2016-0111368, filed Aug. 31, 2016 the contents of each of which are incorporated herein by reference.

TECHNICAL FIELD

The present invention relates to a high internal phase water-in-oil type cosmetic composition, characterized by stabilizing pigments or dyes, which shows colors, in the internal phase part of the high internal phase water-in-oil type cosmetic composition and thus representing the colors of the internal phase when using the product, wherein the high internal phase water-in-oil type cosmetic composition can be used in the manufacture of cosmetic compositions with aesthetic and functional effects and in other similar applications.

BACKGROUND ART

Dry skin is prone to wrinkles and vulnerable to aging. Accordingly, various forms of cosmetic compositions that can supply skin with moisture are available on the market. In particular, recently, a cosmetic product of the high internal phase water-in-oil type emulsion formulation which provides a visual effect such as water droplets bursting out upon application to the skin has been launched to provide a wider range of satisfaction. The high internal phase water-in-oil type emulsion formulation is prepared by significantly increasing the content of the aqueous phase which is the internal phase of the composition particles. In the case of such formulations, when the external stimulus, such as hand rubbing force is applied, the internal phases burst out and coalesce in the form of a water droplet, which is sometimes referred to as the 'water bursting emulsion' because it appears as if the water bursts out and forms a water droplet. This type of emulsion is attracting attention as a new type of moisturizing cosmetics that add fun and psychological satisfaction to product use since the water-containing state can be visually confirmed.

However, the internal phase that bursts out from the conventional high internal phase water-in-oil type emulsion formulation is transparent color, and thus there are considerable limitations in producing various effects other than providing a sense of water. For example, there is a limitation to the applications in the case of expressing the feeling of nourishment in addition to the feeling of moisture or in the case of expressing the characteristics of various functional natural substances contained in the composition and so on by utilizing the characteristics of the internal phase that bursts out during use. Therefore, it is necessary to develop a further improved type of high internal phase water-in-oil type emulsion.

Therefore, the inventors of the present invention have noted that when imparting colors to the internal phase of the emulsion formulation, various functional effects as well as aesthetic effects can be combined, and thus have completed the present invention through long research and efforts.

PRIOR ART LITERATURE

Patent Literature (Patent Literature 1) Water in oil type emulsified cosmetic composition and method of manufacturing the same (Korean Patent No. 10-1453617)

(Patent Literature 2) Water-in-oil type make up cosmetic composition for improving the skin (Korean Laid-open Patent Publication No. 10-2011-0059986)

DISCLOSURE

Technical Problem

The present invention has been made to solve the above problems, and aims at implementing colors in the internal phase of the high internal phase water-in-oil type cosmetic composition. More specifically, it is an object of the present invention to stably maintain a color-exhibiting pigment or dye in the internal phase and to make the colors appear from this when using the product.

In addition, it is another object of the present invention to provide a high internal phase water-in-oil type cosmetic composition in which the colors are implemented in the internal phase which is stably maintained without separation and provide a good degree of surface filling.

Technical Solution

In order to accomplish the above objects, the present invention utilizes a method of solution which includes a color-exhibiting pigment or dye at the time of manufacturing the aqueous phase base which is an internal phase.

In particular, when 'pigment' is included as a material for color implementation, the cosmetic composition of the present invention contains a specific type of emulsifier, which allows the formation of large emulsification particles, so that a color-exhibiting pigment stably exists in the aqueous phase which is the internal phase, and contains a certain kind of dispersant to supplement the emulsifying power and to prevent the separation of the emulsion formulation. In addition, it is preferable that the cosmetic composition contains a thickener to supplementarily stabilize the pigment of the internal phase, silicone oil and ester oil are blended at a suitable ratio to increase the degree of surface filling of the composition, and the content of the dispersant is controlled.

In addition, when 'dye' is used as a material for color implementation, it is particularly not necessary to follow the combination and content of the above-mentioned cosmetic composition, and it can be freely utilized according to the combination and content of the conventional high internal phase water-in-oil type cosmetic composition.

The present invention provides a high internal phase water-in-oil type cosmetic composition comprising any one or more of pigment and dye exhibiting a color to the internal phase and exhibits color of internal phase when using the product.

At this time, the cosmetic composition may comprise at least two emulsifiers selected from the group consisting of PEG-10 dimethicone; lauryl polyglyceryl-3 polydimethylsiloxyethyl dimethicone; lauryl PEG-9 polydimethylsiloxyethyl dimethicone; polyglyceryl-3 polydimethylsiloxyethyl dimethicone; caprylyl methicone, PEG-12 dimethicone/PPG-20 crosspolymer; dimethicone/PEG-10/15 crosspolymer; dimethicone/polyglycerin-3 crosspolymer; cetyl PEG- .PPG-10/1 dimethicone; cetyl dimethicone copolyol; and dimethicone/vinyl dimethicone crosspolymer.

At this time, the cosmetic composition may comprise at least two dispersants selected from the group consisting of polyhydroxy stearic acid; acrylates/ethylhexyl acrylate/dimethicone methacrylate copolymer; and vinylpyrrolidone/hexadecene copolymer.

At this time, the oil phase component of the cosmetic composition may comprise a silicone oil and an ester oil.

At this time, the weight ratio of ester oil to silicone oil may be 1:0.2 or more.

At this time, the color-exhibiting pigments may be at least one selected from the group consisting of pearl particles and an aqueous phase dispersion pigments.

At this time, the pearl particles may be at least one platelet powders selected from the group consisting of mica, synthetic mica, alumina, borosilicate, boron nitride powder, talc and sericite.

At this time, the pearl particles may be one coated with at least one material selected from the group consisting of titanium dioxide, tin oxide and iron oxide.

At this time, the average particle size of the pearl particles may be 6 to 15 μm.

At this time, the aqueous phase dispersion pigments may be titanium dioxide coated with alumina or silica.

At this time, the cosmetic composition may comprise a film former.

At this time, the film former may comprise hydrogenated polycyclopentadiene.

In addition, the present invention provides a high internal phase cosmetic composition including each of silicone oil and ester oil in an amount of 3 to 7% by weight as an oil phase component, relative to the total weight of the composition, including each of dimethicone/PEG-10/15 crosspolymer, dimethicone/polyglycerin-3 crosspolymer and cetyl PEG.PPG-10/1 dimethicone in an amount of 0.1 to 3% by weight as an emulsifier, relative to the total weight of the composition, including each of polyhydroxy stearic acid and acrylates/ethylhexyl acrylate/dimethicone methacrylate copolymer in an amount of 1 to 3% by weight as a dispersant, relative to the total weight of the composition, including any one or more selected from the group consisting of color-exhibiting pigments and dyes in an amount of 1 to 2% by weight as an aqueous phase component, relative to the total weight of the composition, including hydroxyethyl acrylate/sodium acryloyldimethyl taurate copolymer in an amount of 0.01 to 0.5% by weight as a thickener, relative to the total weight of the composition, and including hydrogenated polycyclopentadiene in an amount of 0.1 to 5% by weight as a film former, relative to the total weight of the composition.

Advantageous Effects

The present invention provides a high internal phase water-in-oil type cosmetic composition wherein it implements, when used, colors in the internal phase that forms water droplets on the surface, thereby exhibiting various aesthetic and functional effects, by using the above-mentioned method for solving the problems.

In the case of the cosmetic composition of the present invention, the color-exhibiting pigments or dyes contained in the internal phase remain stably during and after the manufacturing process without separation of the formulation, and when filling the container, the composition is evenly and uniformly filled with respect to its surface.

Accordingly, since both pigments and dyes can be included as the material that implements colors in the internal phase, the cosmetic composition of the present invention makes it possible to provide a wider range of usable color implementation materials through the present invention.

BEST MODE

Figure 1:
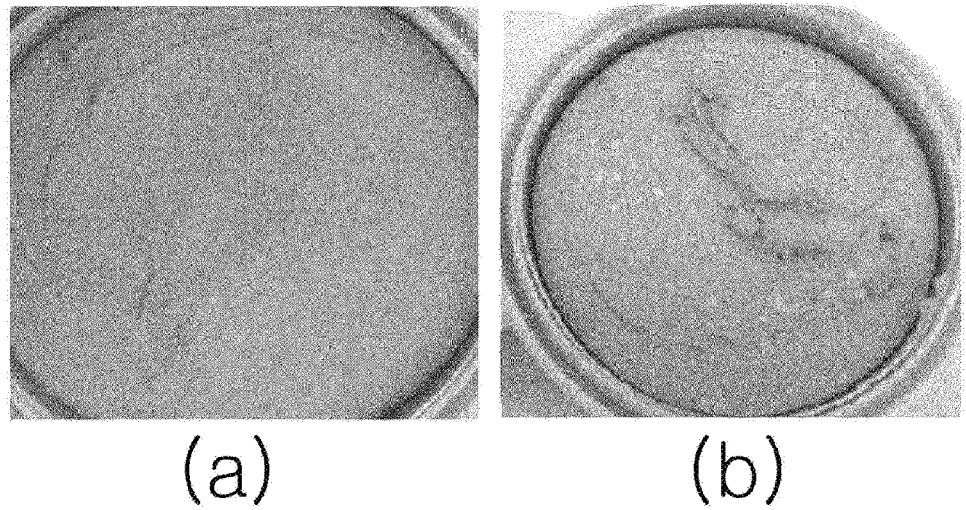
FIG. 1 compares (a) a formulation having a transparent internal phase (conventional emulsion) and (b) a formulation having an internal phase in which the colors are implemented according to the present invention (emulsion of the present invention), in high internal phase water-in-oil type cosmetic composition.

The present invention provides a high internal phase water-in-oil type cosmetic composition that exhibits colors in the internal phase.

The water-in-oil type cosmetic composition with a high internal phase has the property that since the ratio of the internal phase of the water-in-oil type emulsion is increased usually by 20 to 90%, and the size of the emulsification particle is increased, when the external stimulus such as hand rubbing force is applied, the aqueous phase component that constitutes the internal phase comes out and coalesces. The water-in-oil type cosmetic composition is also called 'water bursting' formulation because it looks by the naked eye as if the water bursts out and forms water droplets, which is a formulation that can enhance the user's psychological and aesthetic satisfaction.

The present invention can lead to more various characteristics and effectively highlight the function and purpose of each cosmetic composition by stabilizing the color-exhibiting pigments or dyes in the internal phase of the high internal phase water-in-oil type cosmetic composition.

Among the above color-exhibiting materials, the dye can be freely used in all compositions, while the pigments are difficult to stand alone in a stabilized state in the internal phase and can cause separation of formulations during and after the manufacturing process. Therefore, even when these pigments are included, the present invention provides the combination and content of the most preferred composition to enable the production of a stable cosmetic composition However, it is not intended to limit the cosmetic composition of the present invention to only a specific range, and the cosmetic composition of the specific range should be understood as one implementation means for carrying out the present invention more broadly.

Hereinafter, the present invention will be described in more detail.

However, it is to be understood that the following description merely illustrates the most representative embodiments in order to facilitate understanding of the present invention and thus the scope of the present invention is not limited to the above embodiments, and that the present invention covers all of the equivalent scope of the following description.

The cosmetic composition of the present invention having a color in the internal phase is prepared by the steps comprising preparing and warming an aqueous phase base and an oil phase base; preparing a water-in-oil (W/O) type emulsion by mixing and emulsifying the aqueous phase and the oil phase base; and re-warming for the surface filling of the water-in-oil type emulsion.

In order to prepare the cosmetic composition of the present invention, first, the color-exhibiting pigments or dyes must be stabilized in the aqueous phase, which is the internal phase, in the mixing and emulsifying step, secondly, the emulsified emulsification particles should be formed stably, third, the stability should be maintained without separation of the formulation even at the re-warming step, and fourth, the final surface filling state should be uniform and flat. In particular, the colors are often not realized in the internal phase depending on other component substances contained even though it contains the pearls, color-exhibiting pigments or dyes. However, the present invention proposes a combination and content of component materials, which can stably maintain the pigments in the internal phase, while simultaneously satisfying the above-mentioned requirements.

Specifically, the cosmetic composition of the present invention can satisfy the above-mentioned characteristics required in the production step by including the pearls and the thickener at the time of preparing the aqueous phase base, including a certain type of emulsifier and dispersant at the time of preparing the oil phase base and also limiting the type and blending ratio of the oil constituting the oil phase base.

Hereinafter, each of the core components used in the production of the present invention will be described in more detail.

Color-Exhibiting Pigment and Dye

The present invention is based on adding color-exhibiting pigments or dyes and stabilizing it at the time of preparing the aqueous phase base, in order to embody the colors in the internal phase which forms water droplets when using high internal phase water-in-oil type cosmetic composition. The term 'pigment' as used in the present specification refers to a color as an inorganic substance, and 'dye' means a color-exhibiting material as organic substance.

The pigments may be at least one of pearl particles and aqueous phase dispersion pigments.

The pearl particles are preferably platelet powders such as mica, synthetic mica, alumina, borosilicate, boron nitride powder, talc, or sericite, and it is more preferable to coat the surface thereof with one or a mixture of two or more selected from the group consisting of titanium dioxide, tin oxide and iron oxide. The coating ratio is 2 to 60 wt. % based on the total weight of the pearl particles. In addition, it is preferable that the pearls used in the present invention are a fine interference pearl. The fine interference pearl is white in appearance color. However, since it increases the reflected light on the skin and has a unique interference color, it can show a bright and unique color. The size of the fine interference pearl particles is preferably 6-15 μm in diameter, more preferably 7.19 μm in diameter on average. If the size of the pearl particles is larger than the above range, it is difficult to entrap the particles in the emulsification particle. If the size of the pearl particles is smaller than the above range, the stability of the formulation may deteriorate due to the action at the interface. In other words, since the average particle size of the pearl particles affects the stability of the formulation, excessively large or small pearl particles are not uniformly present in the aqueous phase base and can be demarcated or can act on the interface and thus may degrade the stability of the emulsion.

Conventionally, in contrast to other pigments or dyes, when using particularly the above-mentioned pearl-containing type pigments, there is a difficult limitation to independently stabilize these pigments in the internal phase. This is because titanium dioxide coated on the surface of pearl particles has generally a great tendency to be attracted to the oil phase which is external phase rather than the internal phase when emulsion is formed. However, the present invention can prevent this phenomenon and more stably disperse the pearl pigments in the internal phase by limiting the specific combination and content of the composition.

Meanwhile, the term 'aqueous phase dispersion pigment' as used in the present specification refers to a powder formed by coating an inorganic material with hydrophilic particles. Although the pearl particles are not necessarily excluded from the range of the inorganic substance, it is usually more effective to use the form of utilizing pearl particles than that according to the foregoing, and it is preferable to use other inorganic materials in addition to pearls as the inorganic substance constituting the aqueous phase dispersion pigments. For example, the aqueous phase dispersion pigments of the present invention can be used in the form of titanium dioxide ($TiO_2$) coated with at least one of alumina and silica. The content of the aqueous phase dispersion pigments is preferably 1 to 10% by weight, more preferably 1.5% by weight, relative to the total weight of the composition.

Meanwhile, any dye that can be dispersed in the aqueous phase, such as an organic coloring, can be used as a dye without limitation.

The color-exhibiting pigments or dyes can be selectively or simultaneously used, and the colors realized therefrom can be variously implemented according to the effect to be provided without limitation in any color. For example, a white pearl can be used to express moisturizing, nutritive, or whitening effect generated from milk or essence Emulsifier When the emulsion is emulsified, if the emulsification particles are formed small, the 'water bursting' phenomenon tends to be weakened. Therefore, in the present invention, in order to prevent the above problems and to stably contain the color pigments in the aqueous phase, emulsifiers are used to form large emulsification particles, and among these, certain kinds of emulsifiers are used in combination.

As the emulsifier of the present invention, at least two selected from the group consisting of PEG-10 dimethicone; lauryl polyglyceryl-3 polydimethylsiloxyethyl dimethicone; lauryl PEG-9 polydimethylsiloxyethyl dimethicone; polyglyceryl-3 polydimethylsiloxyethyl dimethicone; caprylyl methicone (and) PEG-12 dimethicone/PPG-20 crosspolymer; dimethicone/PEG-10/15 crosspolymer; dimethicone/polyglycerin-3 crosspolymer; cetyl PEG.PPG-10/1 dimethicone; cetyl dimethicone copolyol; and dimethicone/vinyl dimethicone crosspolymer can be used. Dimethicone/PEG-10/15 crosspolymer, dimethicone/polyglycerin-3 crosspolymer, and cetyl PEG.PPG-10/1 dimethicone can be preferably used.

The content of the emulsifiers is, but is not limited thereto, preferably 0.1 to 3 wt. % relative to the total weight of the composition.

Dispersant

On the other hand, although the pearls may be stabilized in the aqueous phase by the above-mentioned method, since large emulsification particles formed degrade the stability of the formulation or the pigments contained in the aqueous phase affects the stability of the interface, it is easy to cause a problem that the composition is separated during the process. In fact, there arises a problem that the formulation is easily separated during re-warming for filling the composition.

For this purpose, in the case of the present invention, a certain kind of dispersant is added to the oil phase base, and the desired emulsifying retention force and the fluidity of the formulation are supplemented from the dispersant. However, not all dispersants contribute to emulsification. As a dispersant having an emulsifying power suitable for the present invention, two or more selected from polyhydroxy stearic acid, acrylates/ethylhexyl acrylate/dimethicone methacrylate copolymer, and vinylpyrrolidone/hexadecene copolymer can be used, and preferably, polyhydroxy stearic acid and acrylate/ethylhexyl acrylate/Dimethicone methacrylate copolymer can be used.

The content of the dispersant is, but is not limited thereto, preferably 1 to 3 wt. % relative to the total weight of the composition.

Thickener

The thickener can be added to the aqueous phase base to adjunctively prevent the pearls contained in the aqueous phase, which is the internal phase, from being attracted to the oil phase which is the external phase.

When the thickness of the interior increases by adding the thickener, it is also possible that the degree to which the pearls are attracted to the oil phase decreases, and a relatively large amount of pearls are contained compared to the conventional art.

There are no particular restrictions on the type of thickener, but preferably at least one selected from the group consisting of xanthan gum, carbomer, hydroxypropyl starch phosphate, sodium magnesium silicate, hydroxyethyl cellulose, and hydroxyethyl acrylate/sodium acryloyldimethyl taurate copolymer can be used, and the content thereof is preferably 0.01 to 0.5% by weight relative to the total weight of the composition.

Film Former

A film former can be added to give a feeling of close contact on the skin and enhance the sustainability of the makeup.

MQ or T resins such as trimethylsiloxysilicate and polypropyl silsesquioxane, which are commonly used in makeup products, increases the pigment dispersibility in the formulation and disperses color-implementing particles present in the aqueous phase into the oil part. In the case of the present invention, a film former including hydrogenated polycyclopentadiene is used to enhance the adhesion and sustainability without affecting water bursting color.

Combination of Oils

If the final surface filling state is poor, the commercial value of the product is lowered. Therefore, the cosmetic composition of the present invention limits the combination of component materials to ensure an excellent degree of filling.

The degree of filling is affected by the type and blending ratio of oils contained in the oil phase component, and the content of the dispersant which varies depending on the type and blending ratio. Specifically, the oils constituting the oil phase component of the present invention include silicone oil and ester oil, and the higher the blending weight ratio of ester oil to silicone oil, the better the degree of surface filling. This is because as the ester oil compared to silicone oil increases, the size of the emulsification particles increases and thus the high temperature fluidity increases, and as the high temperature fluidity increases, the degree of filling of the formulation becomes better.

In the case of the present invention, when the blending weight ratio of ester oil to silicone oil is 1:0.2 or more, the desired degree of surface filling is obtained.

Taking the above description into consideration, in a preferred embodiment of the present invention, a high internal phase water-in-oil type cosmetic composition, characterized by including each of silicone oil and ester oil in an amount of 3 to 7% by weight as an oil phase component, relative to the total weight of the composition, including each of dimethicone/PEG-10/15 crosspolymer, dimethicone/polyglycerin-3 crosspolymer and cetyl PEG.PPG-10/1 dimethicone in an amount of 0.1 to 3% by weight as an emulsifier, relative to the total weight of the composition, including each of polyhydroxy stearic acid and acrylates/ethylhexyl acrylate/dimethicone methacrylate copolymer in an amount of 1 to 3% by weight as a dispersant, relative to the total weight of the composition, including at least one selected from the group consisting of color-exhibiting pigment sand dyes in an amount of 1 to 2% by weight as an aqueous phase component, relative to the total weight of the composition, including hydroxyethyl acrylate/sodium acryloyldimethyl taurate copolymer in an amount of 0.01 to 0.5% by weight as a thickener, relative to the total weight of the composition, and including hydrogenated polycyclopentadiene in an amount of 0.1 to 5% by weight as a film former, relative to the total weight of the composition, can be prepared.

In addition to the above-mentioned materials, subsidiary component materials may be further contained as long as the effects of the present invention are not impaired.

The water-in-oil type cosmetic composition of the present invention can be any emulsion formulation, but is particularly effective when it is prepared into pact, foundation, cream and the like.

Hereinafter, experimental examples will be described in order to facilitate understanding of the present invention. However, the following experimental examples are only examples of the effects of the present invention, and the scope and effect of the present invention are not limited thereto.

Hereinafter, Example 1 of the present invention and Comparative Examples 1 and 2 will be described. Experimental Examples 1 to 5 relating to the effects of the present invention are also described. The following Example 1 and Comparative Example 1 or 2 were used for the experiment.

Example 1

One embodiment of the prescription of a formulation that implements colors in the internal phase according to the present invention is shown in Table 1 below.

TABLE 1

| Category | Raw material | Content (% by weight) |
|---|---|---|
| Emulsifier | Dimethicone/PEG-10/15 crosspolymer | 1.7% |
| | Dimethicone/polyglycerin-3 crosspolymer | 1.5% |
| | Cetyl PEG•PPG-10/1 dimethicone | 0.1% |
| Oil phase base | Phenyl trimethicone | 7% |
| | Cyclopentasiloxane | 3% |
| | Neopentyl glycol diheptanoate | 5.31% |
| | Ethylhexyl methoxycinnamate | 6% |
| Pigment | Titanium dioxide & zinc oxide & iron oxide | 19% |
| | Pearl pigment (white) | 1.5% |
| Film former | Hydrogenated polycyclopentadiene | 1.5% |
| Dispersant | Acrylates/ethylhexyl Acrylate/dimethicone methacrylate copolymer | 2% |
| | Polyhydroxy stearic acid | 1% |
| Wax | Polyethylene | 3% |
| | Ozokerite | 2% |
| Aqueous phase base | D.I water | to 100 |
| | Polyol (butylene glycol, glycerine) | 12% |
| | Phenoxyethanol | 0.4% |
| | Ethylhexylglycerin | 0.05% |
| | Sodium chloride | 1% |
| | Hydroxyethyl acrylate/sodium Acryloyldimethyl taurate copolymer | 0.1% |

Comparative Example 1

The prescription of a formulation with a transparent internal phase is shown in Table 2 below.

The following prescription is a newly proposed prescription example together with the present invention, and according to this, a formulation of a transparent internal phase can be produced more easily and effectively than the conventional method.

TABLE 2

| Category | Raw material | Content (% by weight) |
|---|---|---|
| Emulsifier | Dimethicone/PEG-10/15 crosspolymer | 1% |
| | Cetyl PEG•PPG-10/1 dimethicone | 0.1% |
| Oil phase base | Phenyl trimethicone | 8% |
| | Cyclopentasiloxane | 3% |
| | Neopentyl glycol diheptanoate | 5.41% |
| | Ethylhexyl methoxycinnamate | 6% |
| Pigment | Titanium dioxide & zinc oxide & iron oxide | 19% |
| Wax | Polyethylene | 3% |
| | Ozokerite | 2% |
| Aqueous phase base | D.I water | to 100 |
| | Polyol (butylene glycol, glycerine) | 12% |
| | Sodium chloride | 1% |

Comparative Example 2

The prescription of a formulation in which the internal phase contains pearls but the colors are not implemented is shown in Table 3 below.

TABLE 3

| Category | Raw material | Content (% by weight) |
|---|---|---|
| Emulsifier | Dimethicone/PEG-10/15 crosspolymer | 1% |
| | Cetyl PEG•PPG-10/1 dimethicone | 0.1% |
| Oil phase base | Phenyl trimethicone | 7% |
| | Cyclopentasiloxane | 3% |
| | Neopentyl glycol diheptanoate | 5.31% |
| | Ethylhexyl methoxycinnamate | 6% |

TABLE 3-continued

| Category | Raw material | Content (% by weight) |
|---|---|---|
| Pigment | Titanium dioxide & zinc oxide & iron oxide | 19% |
| | Pearl pigment (white) | 1.5% |
| Wax | Polyethylene | 3% |
| | Ozokerite | 2% |
| Aqueous phase base | D.I water | to 100 |
| | Polyol (butylene glycol, glycerine) | 12% |
| | Sodium chloride | 1% |

Experimental Example 1: Confirmation of Color Implementation Effect on Internal Phase Comparing Example 1 and Comparative Example 1, the effect of implementing colors in the internal phase can be confirmed.

Referring to FIG. 1, (a) the left side is a formulation having the conventional transparent internal phase prepared according to Comparative Example 1, (b) the right side is a formulation, in which the colors are implemented in the internal phase, as prepared according to Example 1, and (b) it is possible to confirm the internal phases from the right figure, which are burst out in the form of white water droplets.

Experimental Example 2: Confirmation of Specific Effects by Combination of Components In the present invention, in order to impart colors to the internal phase, pearls or aqueous phase pigments are included in the aqueous phase, but according to this, the color implementation depends on the combination of other component materials. In Experimental Example 2, this fact and a combination of components suitable for the present invention were confirmed together by comparing and observing the form of the formulations according to the prescription, FIG. 2 is one of the observation results of Experimental Example 2

Figure 2:
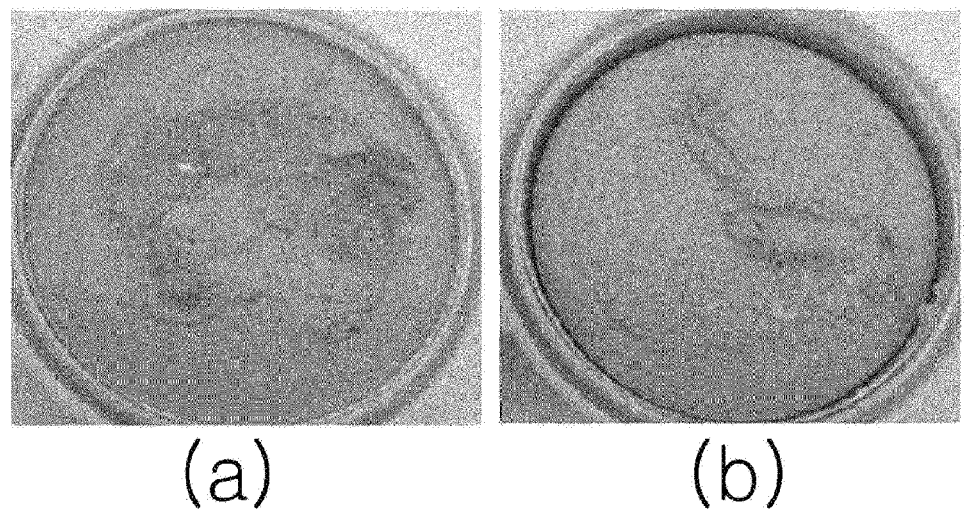
FIG. 2 compares (a) a formulation in which the pearls are included but the colors are not implemented (including pearls, color X) and (b) a formulation in which the colors are implemented according to the present invention (including pearls, color 0), in high internal phase water-in-oil type cosmetic composition.

Referring to FIG. 2, (a) the left side is a formulation prepared according to Comparative Example 2 above, (b) the right side is a formulation prepared according to Example 1 above, and (a) and (b) formulations all contain pearls, it can be confirmed that there is an effect that the colors are implemented only in the right formulation.

It can be seen from Experimental Example 2 that the key element to implementing the present invention lies in the optimal combination of emulsifier, dispersant, thickener and preservative.

Experimental Example 3: Confirmation of the Addition Effect of Dispersant

The addition of a dispersant is essential in the present invention, compared with the formulation of the transparent internal phase.

In Experimental Example 3, the addition effect of the dispersant was confirmed.

Figure 3:
FIG. 3 shows the phenomenon that the formulation in which the addition of a dispersant in the constituent components of the high internal phase water-in-oil type cosmetic composition according to the present invention is omitted is separated during the warming step during the manufacturing process.

FIG. 3 relates to a formulation prepared by omitting the dispersant in the formulation of Example 1 above, and shows the states in which the separation of the formulation has occurred in the re-warming step during the process.

Experimental Example 4: Confirmation of the Degree of Surface Filling Depending on the Combination of Oils In Experimental Example 4, the correlation between the combination of oils in the oil phase component and the degree of surface filling of the composition, and optimal combination of oils to have the desired degree of surface filling were confirmed.

Figure 4:
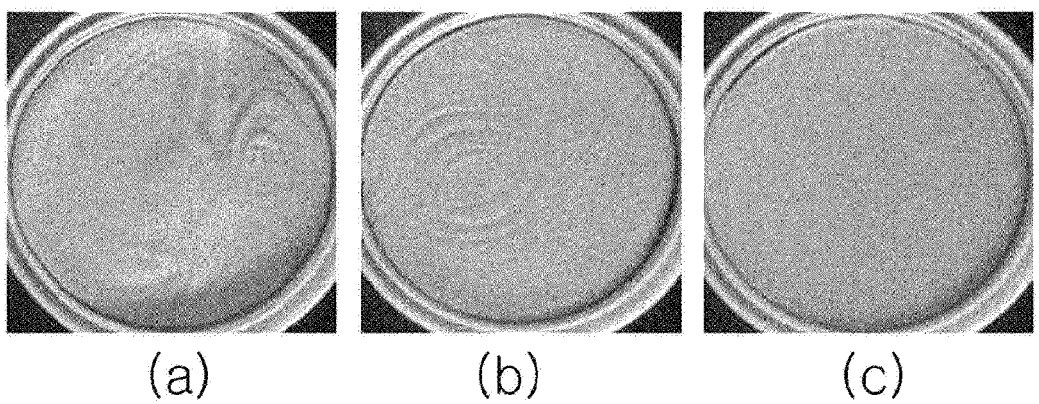
FIG. 4 shows the difference in the degree of surface filling depending on the blend weight ratio of silicone oil and ester oil in the oil component constituting the oil phase base, in high internal phase water-in-oil type cosmetic composition.

Referring to FIG. 4, it can be confirmed that the degree of surface filling can be different by including silicone oil and ester oil as the oil component constituting the oil phase while controlling the weight ratio of the two oils. In FIG. 4, the degree of surface filling is shown (a) when containing 13% of silicone oil and 1.5% of ester oil on the left side, (b) when containing 13% of the silicone oil and 2.56% of the ester oil on the middle side, and (c) when containing 8% of silicone oil and 5.56% of ester oil on the right side. It can be seen that the higher the ratio of ester oil to silicone oil, i.e., the more right-side the formulations, the better the degree of surface filling.

On the other hand, the degree of surface filling is determined depending on the degree of flow of the cosmetic composition at high temperatures. In addition, the high temperature fluidity increases with increasing particle size of the composition.

In this regard, further experiments were conducted to confirm whether the above combination of silicone oil and ester oil affects the high temperature fluidity of the composition.

Figure 5:
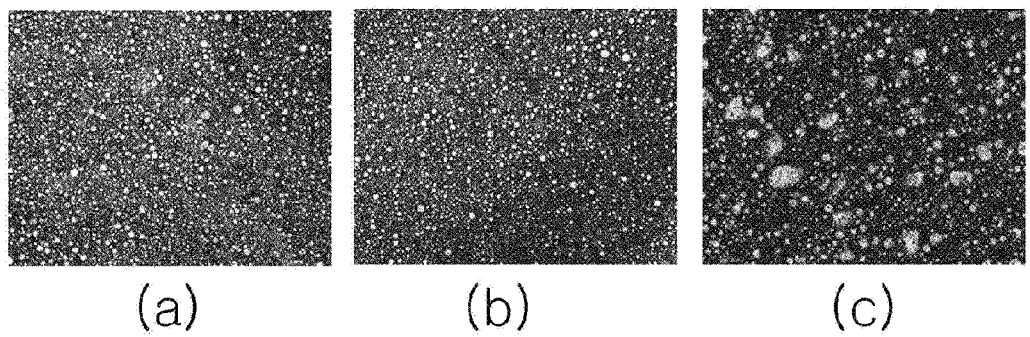
FIG. 5 shows the results of microscopic observation of emulsification particle size of (a) a general formulation, (b) a formulation containing only silicone oil as the oil constituting the oil phase base, and (c) a formulation containing only ester oil as the oil constituting the oil phase base, in high internal phase water-in-oil type cosmetic composition.

FIG. 5 shows the result of observing the particle size of emulsion containing silicone oil or ester oil with a microscope (Eclipse 80i, Nikon Instruments Korea, ×100). In FIG. 5, (a) the left side is a general formulation, (b) the middle side is a formulation containing only silicone oil, and (c) the right is a formulation containing only ester oil. The general formulation refers to a formulation containing 1:1 of ester oil to silicone oil.

Referring to the result of the above observation, it can be seen that the formulation containing only silicone oil do not show a significant difference in particle size compared to the general formulation, but the particle size of the formulation containing only the ester oil is very large. That is, it can be seen that the higher the content of the ester oil, the larger the particle size of the composition, thereby improving the high-temperature flowability and ultimately improving the degree of surface filling.

Experimental Example 5: Confirmation of Characteristics Depending on Average Particle Size of Pearl Particles In the present Experimental Example 5, in order to investigate the effect of particle size of pearl particles on formulation stability and feeling of color, the average particle size of the composition comprising different pearl particles is shown in Table 4 below.

TABLE 4

| | Average particle size | | | |
| --- | --- | --- | --- | --- |
| | 5 µm | 8 µm | 16 µm | 20 µm |
| Characteristics | Formulation separated | Color | Formulation separated | No color |

As shown in table 4, it can be confirmed that if the average particle size of pearl particles is 5 µm and 16 µm, the stability of the formulation deteriorates, and if the average particle size is 20 µm, the colors did not appear. Therefore, it can be seen that the average particle size of the pearl particles is suitably between 6 and 15 µm.

The invention claimed is:

1. A high internal phase water-in-oil type cosmetic composition comprising:
   each of silicone oil and ester oil in the range of 3 to 7% by weight as an oil phase component, relative to the total weight of the composition,
   each of dimethicone/PEG-10/15 crosspolymer, dimethicone/polyglycerin-3 crosspolymer and cetyl PEG/PPG-10/1 dimethicone in the range of 0.1 to 3% by weight as an emulsifier, relative to the total weight of the composition,
   each of polyhydroxy stearic acid and acrylate/ethylhexyl acrylate/dimethicone methacrylate copolymer in the range of 1 to 3% by weight as a dispersant, relative to the total weight of the composition,
   at least one selected from the group consisting of color-exhibiting pigments and dyes in the range of 1 to 2% by weight as an aqueous phase component, relative to the total weight of the composition,
   hydroxyethyl acrylate/sodium acryloyldimethyl taurate copolymer in the range of 0.01 to 0.5% by weight as a thickener, relative to the total weight of the composition, and
   hydrogenated polycyclopentadiene in the range of 0.1 to 5% by weight as a film former, relative to the total weight of the composition.

2. The high internal phase water-in-oil type cosmetic composition of claim 1, wherein the color-exhibiting pigments are at least one of pearl particles and aqueous phase dispersion pigments.

3. The high internal phase water-in-oil type cosmetic composition of claim 2, wherein the pearl particles are at least one platelet powders selected from the group consisting of mica, synthetic mica, alumina, borosilicate, boron nitride powder, talc, and sericite.

4. The high internal phase water-in-oil type cosmetic composition of claim 2, wherein the pearl particles are coated with at least one material selected from the group consisting of titanium dioxide, tin oxide and iron oxide.

5. The high internal phase water-in-oil type cosmetic composition of claim 2, wherein the average particle size of the pearl particles is 6 to 15 µm.

6. The high internal phase water-in-oil type cosmetic composition of claim 2, wherein the aqueous phase dispersion pigments are titanium dioxide coated with alumina or silica.

* * * * *